(12) United States Patent
Kimoto et al.

(10) Patent No.: US 9,498,185 B2
(45) Date of Patent: Nov. 22, 2016

(54) ULTRASOUND DIAGNOSTIC APPARATUS AND ULTRASOUND DIAGNOSTIC SYSTEM

(75) Inventors: Takashi Kimoto, Kanagawa (JP);
Katsumi Satake, Kanagawa (JP);
(Continued)

(73) Assignee: KONICA MINOLTA, INC., Tokyo (JP)

(*) Notice: Subject to any disclaimer, the term of this patent is extended or adjusted under 35 U.S.C. 154(b) by 916 days.

(21) Appl. No.: 13/636,835

(22) PCT Filed: Oct. 27, 2011

(86) PCT No.: PCT/JP2011/006009
§ 371 (c)(1),
(2), (4) Date: Sep. 24, 2012

(87) PCT Pub. No.: WO2012/063420
PCT Pub. Date: May 18, 2012

(65) Prior Publication Data
US 2013/0018263 A1    Jan. 17, 2013

(30) Foreign Application Priority Data
Nov. 12, 2010   (JP) .................. 2010-253738

(51) Int. Cl.
*A61B 8/00*      (2006.01)
*A61B 8/08*      (2006.01)

(52) U.S. Cl.
CPC .......... *A61B 8/4254* (2013.01); *A61B 8/0891* (2013.01); *A61B 8/40* (2013.01); *A61B 8/463* (2013.01);
(Continued)

(58) Field of Classification Search
CPC .............. A61B 19/5244; A61B 2019/504; A61B 2019/507; A61B 8/4254; A61B 5/06; A61B 19/50
See application file for complete search history.

(56) References Cited

U.S. PATENT DOCUMENTS

| 7,074,185 B2 | 7/2006 | Takeuchi |
| 2004/0019270 A1 | 1/2004 | Takeuchi |

(Continued)

FOREIGN PATENT DOCUMENTS

| CN | 1494873 A | 5/2004 |
| CN | 101669831 A | 3/2010 |

(Continued)

OTHER PUBLICATIONS

Chinese Office Action dated Sep. 25, 2014, issued in counterpart Chinese Application No. 201180018233.9.
(Continued)

*Primary Examiner* — Tse Chen
*Assistant Examiner* — Jason Ip
(74) *Attorney, Agent, or Firm* — Holtz, Holtz & Volek PC

(57) ABSTRACT

An ultrasound probe (3) of an ultrasound diagnostic apparatus (1) includes an acceleration sensor (5) provided for outputting acceleration information for use in obtaining an angle of the ultrasound probe at the time of diagnosing a subject. The acceleration information is converted into angle information of the ultrasound probe by an angle conversion section (11). The ultrasound diagnostic apparatus (1) includes a monitor (4) for displaying a diagnosing image of the subject obtained with the ultrasound probe (3), and a body mark (16) corresponding to the diagnostic mode selected at the time of diagnosing and a probe icon (15) placed at an angle corresponding to the angle information with respect to the body mark (16) are displayed on the monitor (4). This makes it possible to provide an ultrasound (Continued)

diagnostic apparatus which can display an angle of the ultrasound probe at the time of diagnosing the subject.

13 Claims, 12 Drawing Sheets

(75) Inventors: Seiichi Fukai, Kanagawa (JP); Satoru Uchikawa, Tokyo (JP); Hajime Hirasawa, Kanagawa (JP); Masao Kimura, Kanagawa (JP)

(52) U.S. Cl.
CPC ............ *A61B 8/467* (2013.01); *A61B 8/5292* (2013.01); *A61B 8/465* (2013.01)

(56) References Cited

U.S. PATENT DOCUMENTS

| | | |
|---|---|---|
| 2005/0119569 A1 | 6/2005 | Ohtake |
| 2007/0010743 A1 | 1/2007 | Arai |
| 2007/0017515 A1* | 1/2007 | Wallace et al. .......... 128/204.23 |
| 2009/0130642 A1* | 5/2009 | Tada et al. ................... 434/262 |
| 2010/0191114 A1 | 7/2010 | Hyun et al. |
| 2010/0222680 A1 | 9/2010 | Hamada |

FOREIGN PATENT DOCUMENTS

| | | | |
|---|---|---|---|
| CN | 101816574 A | | 9/2010 |
| EP | 1684232 A1 | * | 7/2006 |
| JP | 2004-57379 | | 2/2004 |
| JP | 2005-124712 | | 5/2005 |
| JP | 2005270317 A | | 10/2005 |
| JP | 2005270421 A | | 10/2005 |
| JP | 2006192030 A | | 7/2006 |
| JP | 2008-68133 | | 3/2008 |
| JP | 2008149044 A | | 7/2008 |
| JP | 2008-279272 | | 11/2008 |
| JP | 2009-77960 | | 4/2009 |
| JP | 2009-89736 | | 4/2009 |
| JP | 4263579 | | 5/2009 |
| JP | 2009-268735 | | 11/2009 |
| JP | 2010119576 A | | 6/2010 |
| JP | 2010-172701 | | 8/2010 |
| JP | 2010-221011 | | 10/2010 |

OTHER PUBLICATIONS

International Preliminary Report on Patentability issued May 23, 2013 in International (PCT) Application No. PCT/JP2011/006009.
International Search Report issued Dec. 27, 2011 in International (PCT) Application No. PCT/JP2011/006009.
Chinese Office Action (and English translation thereof) dated May 18, 2015, issued in counterpart Chinese Application No. 201180018233.9.
Japanese Office Action (and English translation thereof) dated Jun. 2, 2015, issued in counterpart Japanese Application No. 2012-506240.
Extended European Search Report dated Jul. 23, 2015, issued in counterpart European Application No. 11839185.3.
Chinese Office Action (and English translation thereof) dated Jan. 21, 2016, issued in counterpart Chinese Application No. 201180018233.9.

\* cited by examiner

ULTRASOUND DIAGNOSTIC APPARATUS AND ULTRASOUND DIAGNOSTIC SYSTEM

TECHNICAL FIELD

The present invention relates to an ultrasound diagnostic apparatus having a function of displaying the angle of an ultrasound probe at the time of diagnosing a subject.

BACKGROUND ART

Ultrasound diagnostic apparatuses are medical image apparatuses for irradiating a subject with an ultrasound wave and obtaining tomographic images (diagnosing images) of a soft tissue based on a reflected wave from each tissue in a living body. Because of their high safety, the ultrasound diagnostic apparatuses are widely used for various diagnoses.

In the case of monitoring a lesion over time with reference to diagnosing images acquired with an ultrasound diagnostic apparatus, how the size of a displayed tissue of the lesion and the shape of a periphery of the lesion changed, or how the luminance of the lesion region changed with respect to the surrounding tissue can be determined by comparing a previously acquired diagnosing image (past diagnosing image) with a newly acquired diagnosing image (present diagnosing image) of a same region in a same subject, so that differential diagnosis of whether the lesion is taking a change for the worse or the better can be implemented.

In order to reliably perform the differential diagnosis, it is necessary to acquire the past diagnosing image and the present diagnosing image with the same image quality (including the same position, direction and luminance). It is required, therefore, that an angle of the ultrasound probe in acquiring the past diagnosing image should be identical to an angle of the ultrasound probe in acquiring the present diagnosing image. The angle of the ultrasound probe should preferably be adjusted easily in a short period of time.

Accordingly, an ultrasound diagnostic apparatus has conventionally been proposed which provides a guidance display so that present position and posture of the probe can coincide with the position and posture of the probe in the past diagnosis (see, for example, Patent Literature 1). The conventional ultrasound diagnostic apparatus is structured to measure spatial position and posture of the probe with use of a magnetic sensor provided on the probe and a magnetism generator placed in a bed and the like, to display a registered probe mark based on the measurement data in the past diagnosis while displaying a present probe mark based on the present coordinate data, and to display proximity or coincidence of the registered coordinates and the present coordinates on the guidance display.

For measurement of the spatial position and posture of the probe in the conventional ultrasound diagnostic apparatus, it is necessary not only to provide a magnetic sensor on the probe but also to place a magnetism generator in a bed and the like, i.e., it is necessary to place a large-scale apparatus.

However, in the ultrasound diagnosis, since the ultrasound probe is used in the state of being in contact with a subject, an operator can sensuously understand the positional relation between the ultrasound probe and the subject and does not need the use of such a large-scale apparatus in most cases. For example, measurement of IMT (Intima-Media Thickness) of the carotid artery in arteriosclerosis diagnosis is one of these cases.

Since diagnosis by IMT measurement is conducted by putting an ultrasound probe on the neck surface in advance, an operator can sensuously understand the positional information on the ultrasound probe and the subject and therefore does not need the use of a large-scale apparatus. What is important in the IMT measurement is the angle information of the ultrasound probe which is brought into contact with the subject.

CITATION LIST

Patent Literature

[Patent Literature 1] Japanese Patent No. 4263579

SUMMARY OF INVENTION

Technical Problem

The present invention is invented under the above-mentioned circumstances. An object of the present invention is to provide an ultrasound diagnostic apparatus which can obtain and display the angle of an ultrasound probe at the time of diagnosing a subject without the necessity of placing a large-scale apparatus as in conventional cases.

Solution to Problem

In order to accomplish the above object, an ultrasound diagnostic apparatus of the present invention is structured to include an ultrasound probe; a sensor provided on the ultrasound probe for outputting sensor information for use in obtaining an angle of the ultrasound probe relative to a gravity direction at a time of diagnosing a subject; an angle conversion section for converting the sensor information into angle information of the ultrasound probe; and a display processing section for displaying the angle information on the display section.

As shown in the following description, the present invention includes other aspects. Therefore, the disclosure of the invention is intended to provide a part of the aspects of the present invention, and is not intended to limit the scope of the invention described and claimed herein.

DESCRIPTION OF EMBODIMENTS

Figure 1:
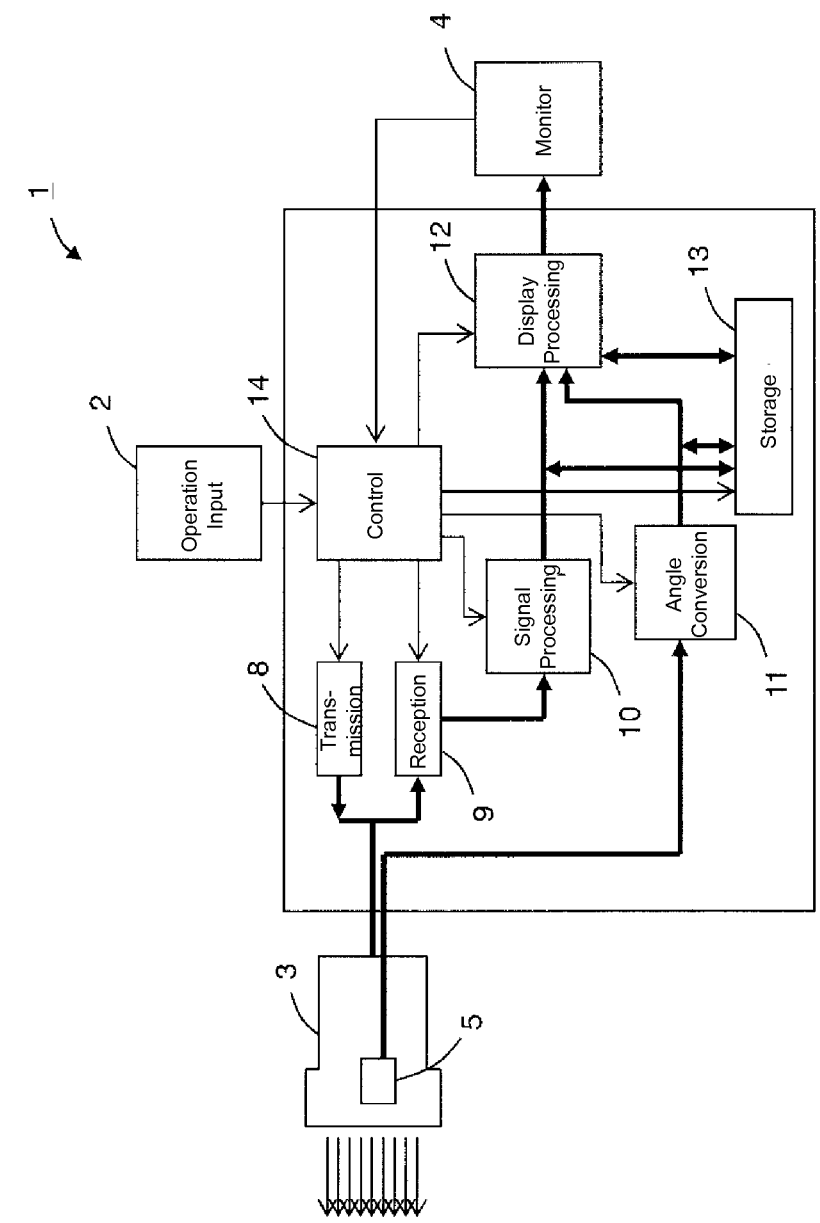
FIG. 1 is a block diagram of an ultrasound diagnostic apparatus in a first embodiment of the present invention.

Hereinafter, the present invention will be described in detail. However, it should be understood that the following detailed description and accompanying drawings are not intended to limit the scope of the present invention.

The ultrasound diagnostic apparatus of the present invention has structure to include: an ultrasound probe; a sensor provided on the ultrasound probe for outputting sensor information for use in obtaining an angle of the ultrasound probe relative to a gravity direction at a time of diagnosing a subject; an angle conversion section for converting the sensor information into angle information of the ultrasound probe; and a display processing section for displaying the angle information on a display section.

The display processing section may have structure to display on the display section angle information as an angle of the ultrasound probe relative to the subject.

Further, the ultrasound diagnostic apparatus may have structure to include an image generation section for generating a probe image indicating the ultrasound probe as a schematic graphic and a subject image indicating the subject as a schematic graphic, in which the display processing section displays the subject image and the probe image on the display section and places the probe image at an angle corresponding to the angle information in a region having a specified positional relation with the subject image.

Furthermore, the display processing section may have structure to display an angle corresponding to the angle information by a direction of the probe image.

Moreover, the display processing section may have structure to set the region over the subject image and to display the probe image as if in contact with the subject image on the display section.

Further, the ultrasound diagnostic apparatus may have structure to include a diagnostic mode selection section for selecting a diagnostic mode for diagnosing the subject with the ultrasound probe.

With these structures, the sensor information outputted from the sensor provided on the ultrasound probe is converted into angle information, so that an angle of the ultrasound probe at the time of diagnosing the subject can be obtained and displayed on the display section without the necessity of a large-scale apparatus as in conventional cases (e.g., a magnetic field generator which cannot be mounted on the probe and can only be mounted on the bed). In the case of the present invention, a subject image (body mark) corresponding to the diagnostic mode selected by a user (such as doctors and engineers) and a probe image (probe icon) placed at an angle corresponding to the angle information with respect to the subject image are displayed on the display section where diagnosing images are displayed. Accordingly, the user can sufficiently acquire information required for diagnosis from these images (images displayed on the display section).

The ultrasound diagnostic apparatus of the present invention may have structure so that the sensor is an acceleration sensor for outputting acceleration information of the ultrasound probe as information for use in obtaining the angle of the ultrasound probe, and the angle conversion section converts the acceleration information into angle information of the ultrasound probe.

With this structure, the acceleration information outputted from the acceleration sensor provided on the ultrasound probe is converted into angle information, so that an angle of the ultrasound probe at the time of diagnosing the subject may be acquired. The acceleration sensor is suitable to be mounted on the ultrasound probe as it does not require a large-scale apparatus as in conventional cases (e.g., a magnetic field generator which cannot be mounted on the probe and can only be mounted on the bed) and it is easy to downsize.

The ultrasound diagnostic apparatus of the present invention may have structure so that the display processing section displays on the display section a button image whose button name is changed in sequence in dependence with diagnostic procedures of the subject.

With this structure, the button name of the button image (workflow button) displayed on the display section is changed in sequence in accordance with the diagnostic procedures of the subject, so that the user can implement the diagnostic procedures easily and appropriately with use of one button (workflow button).

The ultrasound diagnostic apparatus of the present invention may have structure so that once a diagnostic procedure indicated by the button name is completed, the display processing section displays on the display section a button image representing a subsequent diagnostic procedure in a blinking state.

With this structure, once the diagnostic procedure shown with the button image (workflow button) on the display section is completed, the button (workflow button) is changed to represent a subsequent diagnostic procedure and is also displayed in a blinking state. This makes it possible to guide the user to proceed to the next diagnostic procedure.

The ultrasound diagnostic apparatus of the present invention may have structure to include: a storage section for storing image data on a diagnosing image of the subject; and a storage processing section for associating, when the diagnostic mode of the subject shifts to a subsequent diagnostic mode, image data on the diagnosing image obtained in the diagnostic mode prior to mode shift with the angle information and storing the associated image data and angle information in the storage section.

With this structure, when one diagnostic mode shifts to another diagnostic mode, the image data on the diagnosing image obtained in the one diagnostic mode (diagnostic mode prior to mode shift) is associated with the angle information and this associated image data and angle information are stored. Therefore, in the case of referring to the past diagnosing image (diagnosing image obtained in the diagnostic mode) such as in the case of progress observation of the diagnostic region for example, the angle information at the time when the diagnosing image was obtained can be acquired together with the image, and this allows contrast observation with use of the images obtained under the same conditions (in the same diagnostic mode and at the same angle).

The ultrasound diagnostic apparatus of the present invention may have structure so that when displaying the probe image on the display section, the display processing section displays a reference probe image in distinction from the probe image, the reference probe image being displayed at an angle corresponding to the angle information of a past read from the storage section.

With this structure, when the present probe image (probe icon) is displayed and if the same diagnostic mode has been used for diagnosis before, then a reference probe image (reference probe icon) used for obtaining the diagnosing image in the past diagnosis is displayed together with the present probe image. In this case, the reference probe image (reference probe icon) and the present probe image (probe icon) are displayed with their configurations different from each other (such as different color and shape), so that the user can easily distinguish one from the other. The user can conduct diagnosis under the conditions same as the past diagnosis (in the same diagnostic mode and at the same angle) by making the reference probe image (reference probe icon) and the present probe image (probe icon) coincide with each other.

The ultrasound diagnostic apparatus of the present invention may have structure so that when past angle information is not stored in the storage section, the display processing section displays the reference probe image on the display section at a recommended angle preset corresponding to the diagnostic mode.

With this structure, when a given subject has never been diagnosed in the same diagnostic mode before, a reference probe image (reference probe icon) is displayed at a recommended angle preset corresponding to the diagnostic mode (appropriate angle corresponding to the diagnostic mode). Therefore, the user can conduct diagnosis under appropriate conditions corresponding to the diagnostic mode by making the reference probe image (reference probe icon) and the present probe image (probe icon) coincide with each other.

The ultrasound diagnostic apparatus of the present invention may have structure so that the display processing section displays on the display section a guide image indicating a direction to incline the ultrasound probe in the diagnostic mode, and when past angle information is stored in the storage section, the guide image is generated based on the past angle information read from the storage section and present angle information converted from the sensor information, whereas when the past angle information is not stored in the storage section, the guide image is generated based on a recommended angle preset corresponding to the diagnostic mode and the present angle information converted from the sensor information.

With this structure, a guide image indicating a direction to incline the ultrasound probe in the diagnostic mode is displayed on the display section. When the past angle information is stored in the storage section, the guide image is appropriately generated based on the past angle information and the present angle information. Therefore, the user can easily conduct diagnosis under the conditions same as the past diagnosis (in the same diagnostic mode and at the same angle) according to the guide image. When the past angle information is not stored in the storage section, the guide image is appropriately generated based on the recommended angle preset corresponding to the diagnostic mode (appropriate angle corresponding to the diagnostic mode) and the present angle information. Therefore, the user can easily conduct diagnosis under the appropriate conditions corresponding to the diagnostic mode according to the guide image.

The ultrasound diagnostic apparatus of the present invention may have structure so that the display processing section displays on the display section an animation picture for guiding a diagnostic procedure of the subject in the diagnostic mode, and once the diagnostic procedure guided with the animation picture is completed, the display processing section displays an animation picture for guiding a subsequent diagnostic procedure.

With this structure, an animation picture for guiding a diagnostic procedure of the subject is displayed on the display section. Once the diagnostic procedure guided with the animation picture is completed, an animation picture for guiding a subsequent diagnostic procedure is displayed. The user can implement the diagnostic procedures easily and appropriately according to the animation picture.

The ultrasound diagnostic apparatus of the present invention may have structure so that when displaying past diagnosing image stored in the storage section, the display processing section displays on the display section past angle information stored in association with the past diagnosing image.

With this structure, when the past diagnosing image (cine image) is displayed on the display section, the past angle information stored in association with the past diagnosing image is displayed. Therefore, the user can see the angle information in the past diagnosis together with the diagnosing image obtained at the time of the past diagnosis.

The ultrasound diagnostic apparatus of the present invention may have structure to include a diagnostic mode determination section for performing image analysis of the diagnosing image to determine a diagnostic mode in which the diagnosing image was obtained, in which the display processing section displays on the display section a probe image corresponding to the diagnostic mode determined in the diagnostic mode determination section.

With this structure, through image analysis of the diagnosing image, the diagnostic mode in which the diagnosing image was obtained is automatically determined, and an appropriate probe image (probe icon) corresponding to the diagnostic mode is displayed on the display section. For example, when it is determined as a result of conducting image analysis of the diagnosing image that the diagnostic mode is "plaque search", then the probe image (probe icon) for "plaque search" is displayed. When it is determined as a result of conducting image analysis of the diagnosing image that the diagnostic mode is "IMT (Intima-Media Thickness) measurement", then the probe image (probe icon) for "IMT measurement" is displayed.

The ultrasound diagnostic apparatus of the present invention may have structure to include a diagnostic mode determination section for performing image analysis of the diagnosing image to determine a diagnostic mode in which the diagnosing image was obtained, in which the storage section includes a storage area where image data on the diagnosing image and the angle information are stored per diagnostic mode of the subject, and the storage processing section distributes and stores the image data on the diagnosing image and the angle information in the storage area corresponding to the diagnostic mode determined in the diagnostic mode determination section.

With this structure, through the image analysis of the diagnosing image, the diagnostic mode in which the diagnosing image was obtained is automatically determined, and the image data on the diagnosing image and the angle information are distributed and stored in an appropriate storage area corresponding to the diagnostic mode. For example, when it is determined as a result of conducting image analysis of the diagnosing image that the diagnostic mode is "plaque search", then the image data on the diagnosing image and the angle information are stored in the storage area for "plaque search". Moreover, when it is determined as a result of conducting image analysis of the diagnosing image that the diagnostic mode is "IMT measurement" for example, then the image data on the diagnosing image and the angle information are stored in the storage area for "IMT measurement".

The ultrasound diagnostic apparatus of the present invention may have structure so that the display section is a touch panel, and selection of the diagnostic mode is achieved by touch operation on the touch panel.

With this structure, the display section and the diagnostic mode selection section are configured as a touch panel, so that the operability in selecting diagnostic mode is enhanced.

An ultrasound diagnostic system of the present invention has structure to include: an ultrasound probe; a sensor provided on the ultrasound probe for outputting sensor information for use in obtaining an angle of the ultrasound probe at a time of diagnosing a subject; an angle conversion section for converting the sensor information into angle information of the ultrasound probe; an image generation section for generating a probe image indicating the ultrasound probe as a schematic graphic and a subject image indicating the subject as a schematic graphic; and a display processing section for displaying the subject image and the probe image on a display section and using the angle information as an angle of the ultrasound probe with respect to the subject to place the probe image at an angle corresponding to the angle information in a region having a specified positional relation with the subject image.

According to the system, as in the above-stated apparatus, an angle of the ultrasound probe at the time of diagnosing the subject can be obtained and displayed on the display section without the necessity of a large-scale apparatus as in conventional cases (e.g., a magnetic field generator which cannot be mounted on the probe and can only be mounted on the bed), and the user can sufficiently acquire information required for diagnosis from the images displayed on the display section.

The ultrasound diagnostic system of the present invention may have structure to include an ultrasound diagnostic apparatus; and a server apparatus communicably connected with the ultrasound diagnostic apparatus, in which the server apparatus includes a storage section for storing image data on a diagnosing image of the subject, and the ultrasound diagnostic apparatus includes a storage processing section for associating, when a diagnostic mode of the subject shifts to a subsequent diagnostic mode, image data on the diagnosing image obtained in the diagnostic mode prior to mode shift with the angle information, transmitting the associated image data and angle information to the server apparatus, and storing the associated image data and angle information in the storage section of the server apparatus.

With this structure, when one diagnostic mode shifts to another diagnostic mode, the image data on the diagnosing image obtained in the one diagnostic mode (diagnostic mode prior to mode shift) are associated with the angle information, and this associated image data and angle information are transmitted from the ultrasound diagnostic apparatus to the server apparatus and stored in the storage section of the server apparatus. Therefore, in the case of referring to the past diagnosing image (diagnosing image obtained in the diagnostic mode) such as in the case of progress observation of the diagnostic region for example, the ultrasound diagnostic apparatus can acquire the angle information at the time when the diagnosing image was obtained together with the image from the storage section of the server apparatus, and this allows contrast observation with use of the images obtained under the same conditions (in the same diagnostic mode and at the same angle).

The present invention makes it possible to obtain and display the angle of an ultrasound probe at the time of diagnosing the subject without the necessity of placing a large-scale apparatus as in conventional cases.

Hereinafter, the ultrasound diagnostic system in an embodiment of the present invention will be described with reference to the drawings. In this embodiment, the case of the ultrasound diagnostic system for use in the medical field is taken as an example.

(First Embodiment)

The structure of the ultrasound diagnostic apparatus in the first embodiment of the present invention is described with reference to the drawings. FIG. 1 is a block diagram showing the structure of the ultrasound diagnostic apparatus of the present embodiment. As shown in FIG. 1, the ultrasound diagnostic apparatus 1 includes an operation input section 2, an ultrasound probe 3, and a monitor 4 (display section). The operation input section 2 is a console including, for example, a keyboard, a mouse, operation buttons, and a trackball. The operation input section 2 is used for performing operations such as various kinds of information input and command input, and setting and change of parameter information. The ultrasound probe 3 is an ultrasound probe which irradiates a subject with an ultrasound pulse from an ultrasound transducer (not shown), receives reflected ultrasound from each tissue in the living body, and converts the reflected ultrasound into an electrical signal. The ultrasound probe 3 is equipped with an acceleration sensor 5 which outputs acceleration information (information on gravitational acceleration) of the ultrasound probe 3 at the time of diagnosing the subject. A diagnosing image 6 of the subject obtained with the ultrasound probe 3 is displayed on the monitor 4 (see FIG. 2 and other drawings). The monitor 4 is constituted from a touch panel having a function of selecting a diagnostic mode for diagnosing the subject with the ultrasound probe 3 by touch operation.

Figure 2:
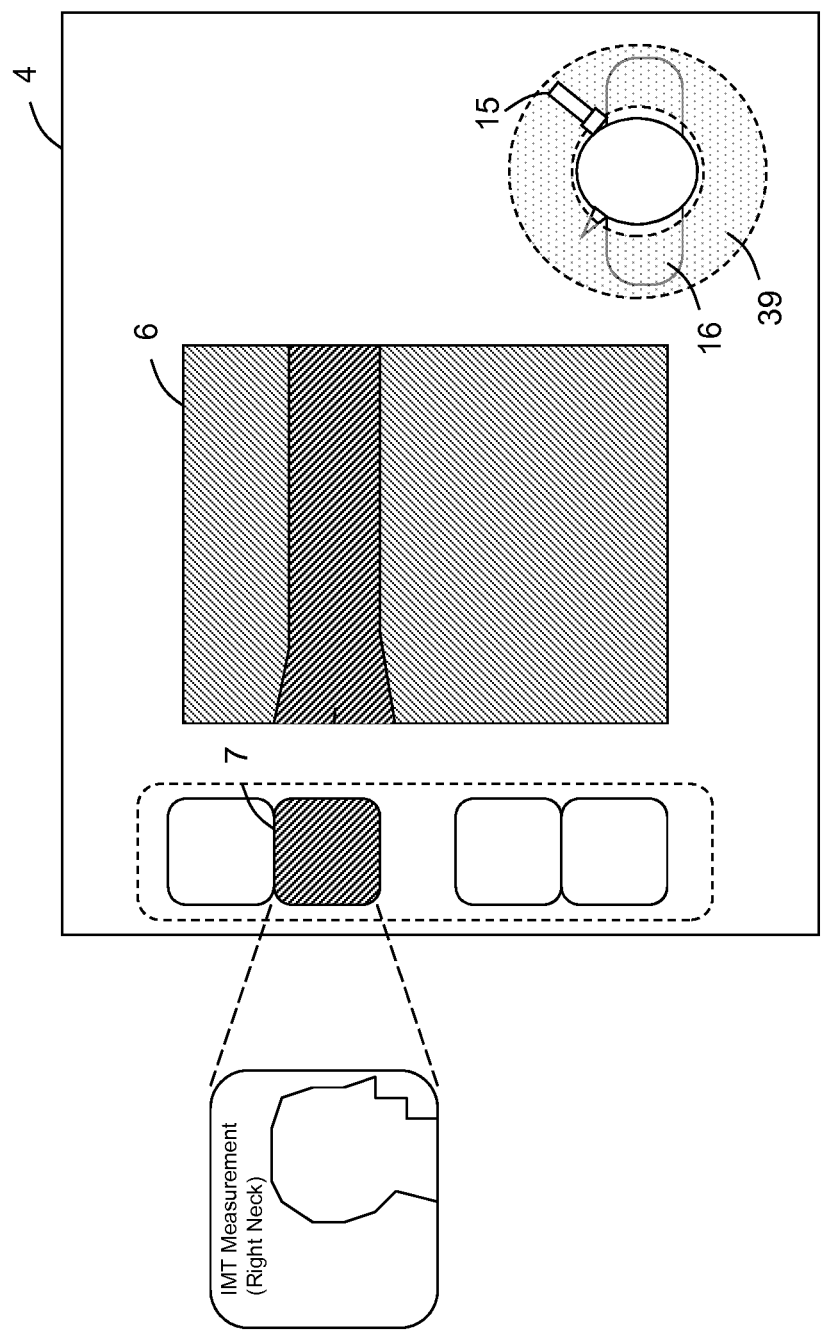
FIG. 2 is an explanatory view of a display screen at the time of IMT measurement.
Figure 3:
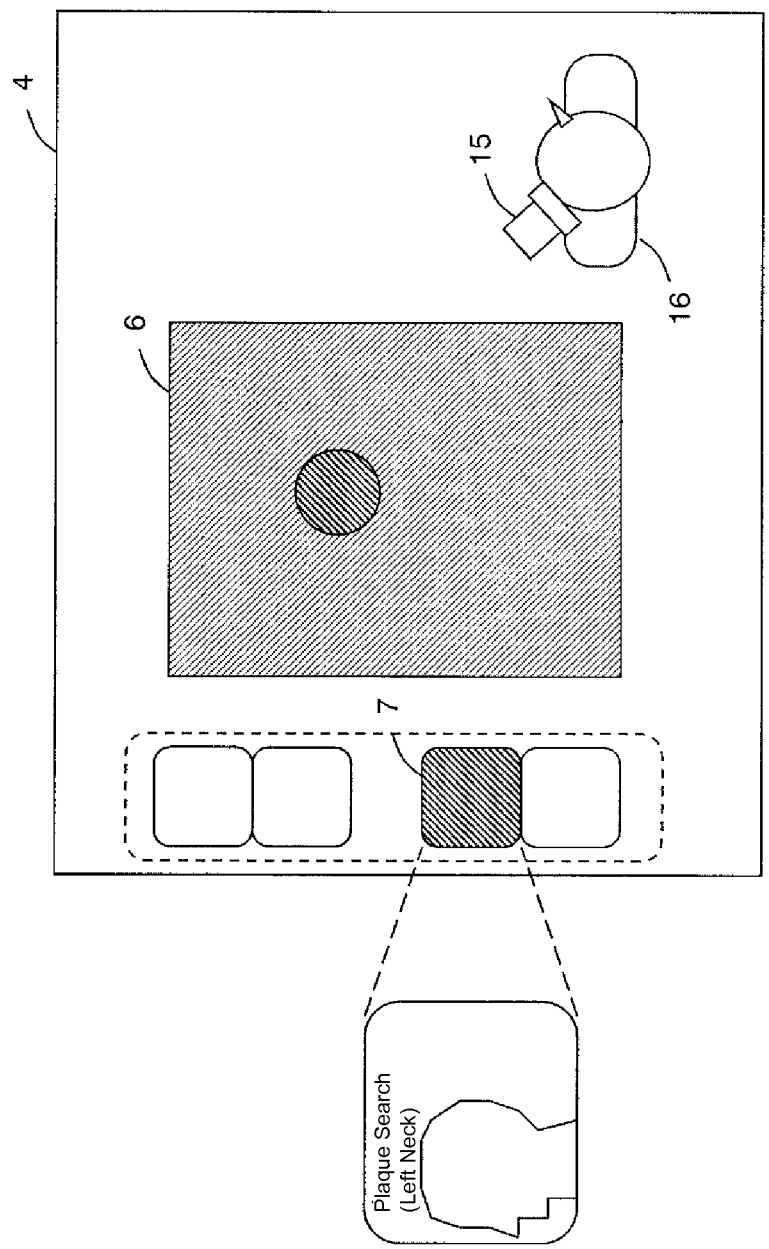
FIG. 3 is an explanatory view of the display screen at the time of plaque search.

The diagnostic mode includes, for example, "plaque search (right neck)", "IMT measurement (right neck)", "plaque search (left neck)", and "IMT measurement (left neck)". As shown in FIG. 2 and FIG. 3, diagnostic mode buttons 7 corresponding to respective diagnostic modes are displayed at the left end of the display screen of the monitor 4, and a user (such as doctors and engineers) can select one (or a plurality) of these buttons by touch operation. In a whole diagnostic mode where all the diagnostic modes are performed, the diagnostic modes of "plaque search (right neck)", "IMT measurement (right neck)", "plaque search (left neck)", and "IMT measurement (left neck)" are shifted in sequence in this order.

The diagnostic mode may automatically be judged (determined) by conducting image analysis of the diagnosing image 6. For example, when a diagnosing image 6 indicating the cross section in a longitudinal direction of the carotid artery is obtained as shown in FIG. 2, the diagnostic mode is determined to be "IMT measurement", whereas when a diagnosing image 6 indicating the cross section which looks like a round slice of the carotid artery is obtained as shown in FIG. 3, the diagnostic mode is determined to be "plaque search."

The ultrasound diagnostic apparatus 1 also includes a transmission section 8 which transmits a transmission signal to irradiate the ultrasound probe 3 with an ultrasound pulse, a reception section 9 which receives a reception signal (an electrical signal formed by converting reflected ultrasound) outputted from the ultrasound probe 3, and a signal processing section 10 which performs specified signal processing on the signal outputted from the reception section 9. The ultrasound diagnostic apparatus 1 also includes an angle conversion section 11 which converts the acceleration information outputted from the acceleration sensor 5 of the ultrasound probe 3 into angle information of the ultrasound probe 3 (information on a three-dimensional angle of the ultrasound probe 3 at the time of diagnosing the subject), and a display processing section 12 which performs various processing steps (described later) for displaying images on the monitor 4.

It is to be noted that the conversion of the acceleration information into the angle information is achieved by calculating respective axial angles of a triaxial acceleration sensor with respect to the gravitational acceleration direction based on acceleration data on respective axes with respect to the gravitational acceleration to derive angle data of the triaxial acceleration sensor and by adding the information on a mounting position relation between the triaxial acceleration sensor and the ultrasound probe 3 to the derived angle data, as a result of which the acceleration information is converted into the angle information of the ultrasound probe 3. The acceleration information may be converted into the angle information in the methods other than the method disclosed in this embodiment, such as a method involving a gyroscope added to the triaxial acceleration sensor and a method using a six-axis sensor. The present embodiment is structured with the triaxial acceleration sensor since the general positional relation between the subject and the probe in each diagnostic mode is assumable in the operation therein.

Further, the ultrasound diagnostic apparatus 1 includes a storage section 13 constituted from a device such as high-capacity HDDs and memories and a control section 14 constituted from a device such as CPUs and microcomputers. The image data on the diagnosing image 6 of the subject is stored in the storage section 13 in association with the angle information. In the present embodiment, when the diagnostic mode of the subject shifts to a subsequent diagnostic mode, image data on the diagnosing image 6 obtained in the diagnostic mode prior to mode shift is associated with the angle information and stored in the storage section 13. Each section of the ultrasound diagnostic apparatus 1 is controlled by the control section 14. The control section 14 may include functions of image analysis of the diagnosing image 6 and diagnostic mode determination. The storage section 13 may include a storage area where image data on the diagnosing image 6 and the angle information are stored per diagnostic mode of the subject, and the image data on the diagnosing image 6 and the angle information may automatically be distributed and stored in the storage area corresponding to the diagnostic mode determined in the image analysis of the diagnosing image 6.

The display processing section 12 has a function of generating a probe image 15 (probe icon 15) indicating the ultrasound probe 3 as a schematic graphic and a subject image 16 (body mark 16) indicating the subject as a schematic graphic, and displaying the body mark 16 and the probe icon 15 corresponding to the diagnostic mode on the monitor 4. In this case, the body mark 16 is displayed at a specified position on the monitor 4, while the probe icon 15 is displayed within a display area 39 having a specified positional relation with the body mark 16. The angle of the ultrasound probe 3 calculated with respect to the gravitational acceleration direction from the angle conversion section 11 is regarded as an angle of the ultrasound probe 3 with respect to the subject, and the probe icon 15 is placed at an angle corresponding to the angle information. In the first Embodiment, the angle information is displayed by the position and direction of the probe icon 15 placed within the display area. Moreover, setting the display area 39 over or in the vicinity of the body mark 16 and displaying the probe icon 15 as if in contact with the body mark 16 on the monitor 4 make it possible to provide the structure enabling an operator to easily imagine the angle information of the ultrasound probe 3.

It is to be noted that the display processing section 12 may display the body mark 16 and the probe image corresponding to the diagnostic mode selected by the user by touch operation, or may display the body mark 16 and the probe image corresponding to the diagnostic mode determined by the image analysis of the diagnosing image 6.

For example, FIG. 2 is a view showing an example of the display screen of the monitor 4 at the time of IMT measurement of the right neck. In this case, the display area 39 is set around the vicinity of the head of the body mark 16. As shown in FIG. 2, displayed on the display screen of the monitor 4 are the body mark 16 corresponding to the diagnostic mode of "IMT measurement (right neck)" (body mark 16 indicating the subject with his/her neck inclined to the left as seen from the overhead), and the probe icon 15 corresponding to the diagnostic mode of "IMT measurement (right neck)" (probe icon 15 indicating the probe in the state of being applied sideways along the carotid artery).

FIG. 3 is a view showing an example of the display screen of the monitor 4 at the time of plaque search of the left neck. As shown in FIG. 3, displayed on the display screen of the monitor 4 are the body mark 16 corresponding to the diagnostic mode of "plaque search (left neck)" (body mark 16 indicating the subject with his/her neck inclined to the right as seen from the overhead), and the probe icon 15 corresponding to the diagnostic mode of "plaque search (left neck)" (probe icon 15 indicating the probe in the state of being applied vertically with respect to the carotid artery).

Figure 4:
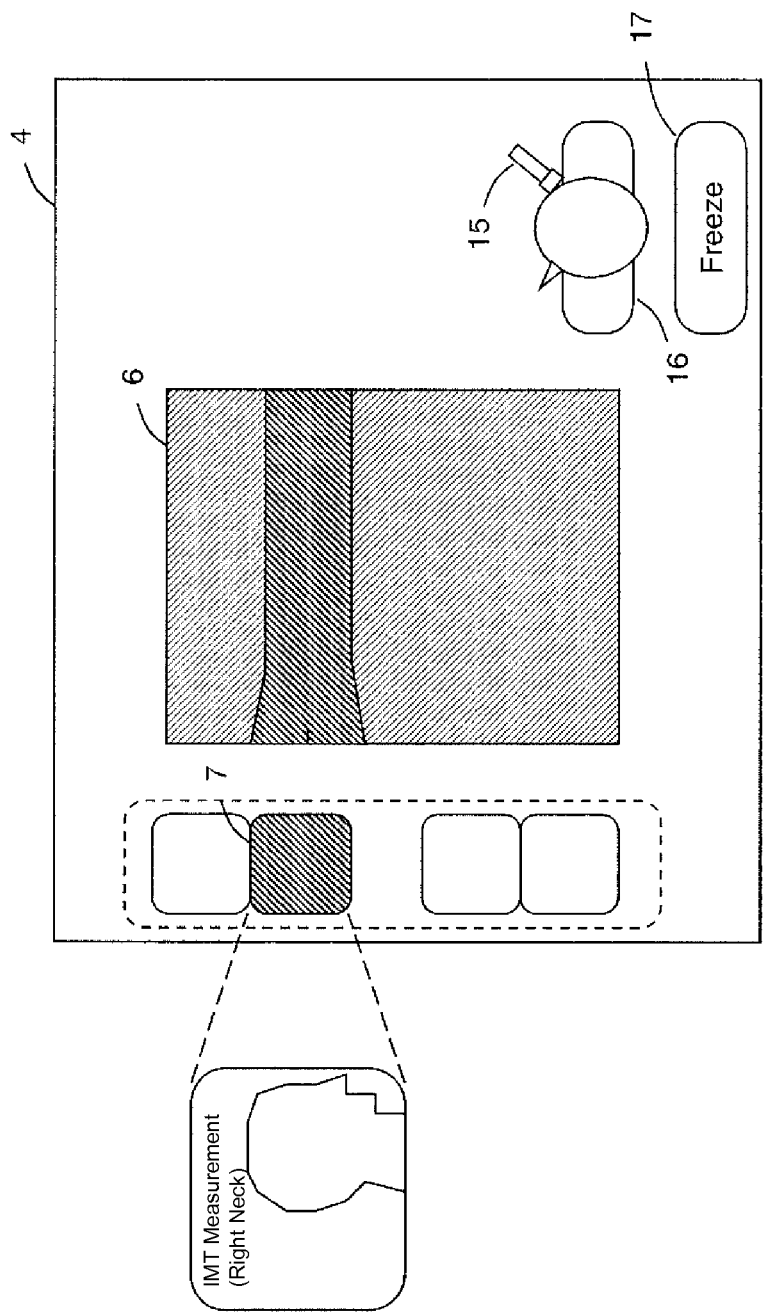
FIG. 4 is an explanatory view of a workflow button.

The display processing section 12 also has a function of displaying on the monitor 4 a button image (workflow button 17) whose button name is changed in sequence in accordance with the diagnostic procedures of the subject. An example of the workflow button 17 is shown in FIG. 4. Although the button indicating "freeze" is displayed in the example of FIG. 4, the display is changed in sequence in accordance with the diagnostic procedures. For example, when the whole diagnostic mode is performed, the display of the workflow button 17 is changed in order of "plaque search (right neck)", "freeze", "IMT measurement (right neck)", "freeze", "plaque search (left neck)", "freeze", "IMT measurement (left neck)", and "freeze". Once the diagnostic procedure (e.g., plaque search (right neck)) displayed in the workflow button 17 is completed, the subsequent diagnostic procedure (e.g., freeze) is displayed in the workflow button 17 and also the workflow button 17 is put in a blinking state (see FIG. 6).

At this point, touching the workflow button 17 in the blinking state makes it possible to proceed to the subsequent diagnostic procedure.

It is to be noted that whether or not the analysis of the displayed diagnosing image is completed is determined by comparing the displayed diagnosing image with a diagnosing image acquired in the past or an image stored as a reference image, i.e., if the displayed diagnosing image is within an optionally set condition range, the diagnostic procedure is determined to be completed, and the apparatus is set to proceed to the subsequent diagnostic procedure based on this determination.

Further, the display processing section 12 has a function of displaying on the monitor 4 a guide image 18 indicating a direction to incline the ultrasound probe 3 in the diagnostic mode. When past angle information is stored in the storage section 13, the guide image 18 is generated based on the past angle information (past angle information read from the storage section 13) and present angle information (present angle information converted from the acceleration information). When the past angle information is not stored in the storage section, the guide image is generated based on a recommended angle preset corresponding to the diagnostic mode and the present angle information (present angle information converted from the acceleration information).

Figure 5:
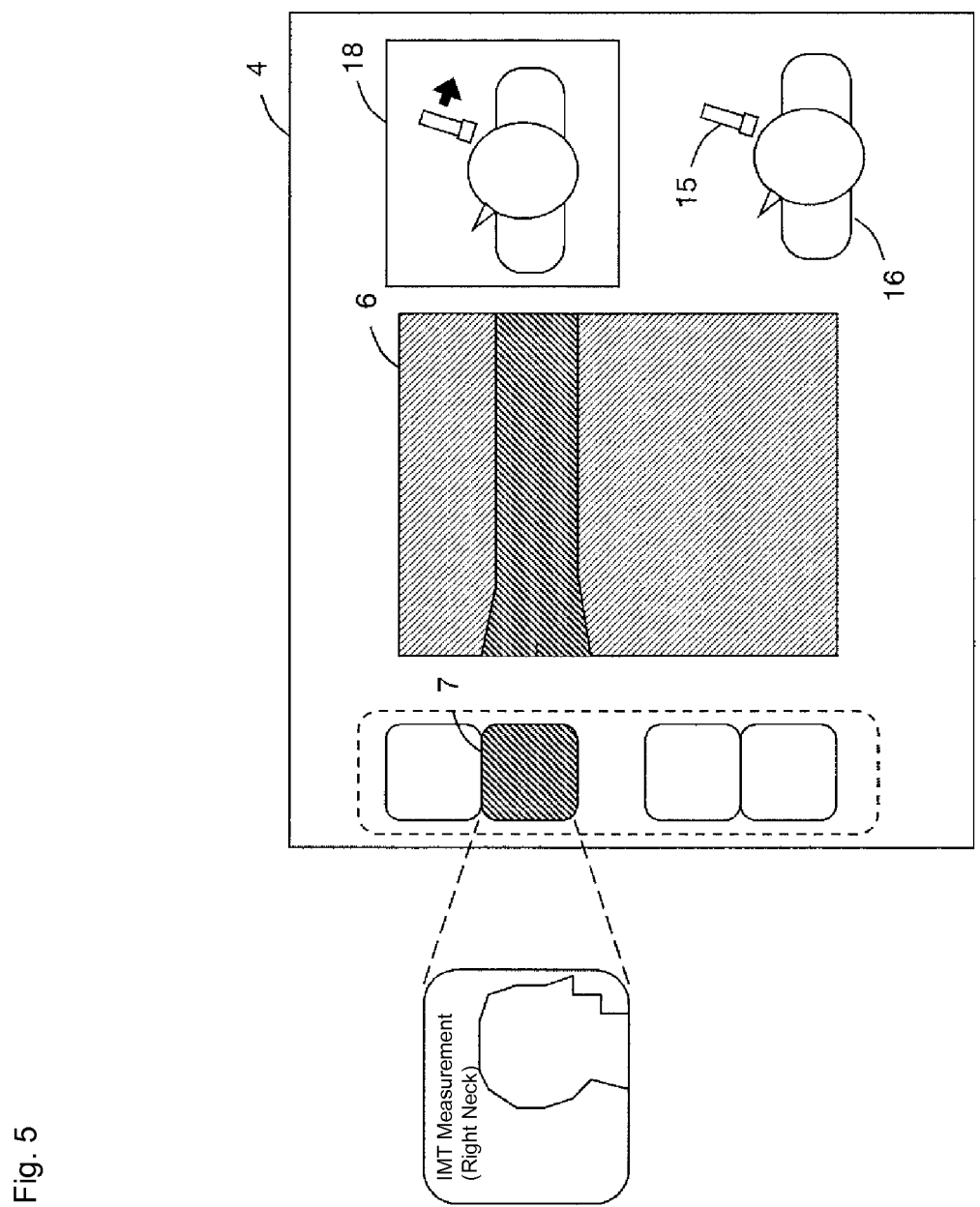
FIG. 5 is an explanatory view of a guide image.

An example of the guide image 18 is shown in FIG. 5. In the example of FIG. 5, the probe icon 15 is displayed at an angle corresponding to the present angle information, while the direction to incline the probe icon 15 (ultrasound probe 3) is shown with an "arrow". The direction of the "arrow" is determined based on the past angle information (or preset recommended angle). More specifically, the direction of the "arrow" is set so that the present angle information coincides with the past angle information (or preset recommended angle). Further, the arrow may display not only the direction but also the difference between the present angle information and the past angle information, i.e., a longer or thicker arrow may indicate a larger difference to provide operational support for the user to recognize a degree of the difference by intuition.

Figure 6:
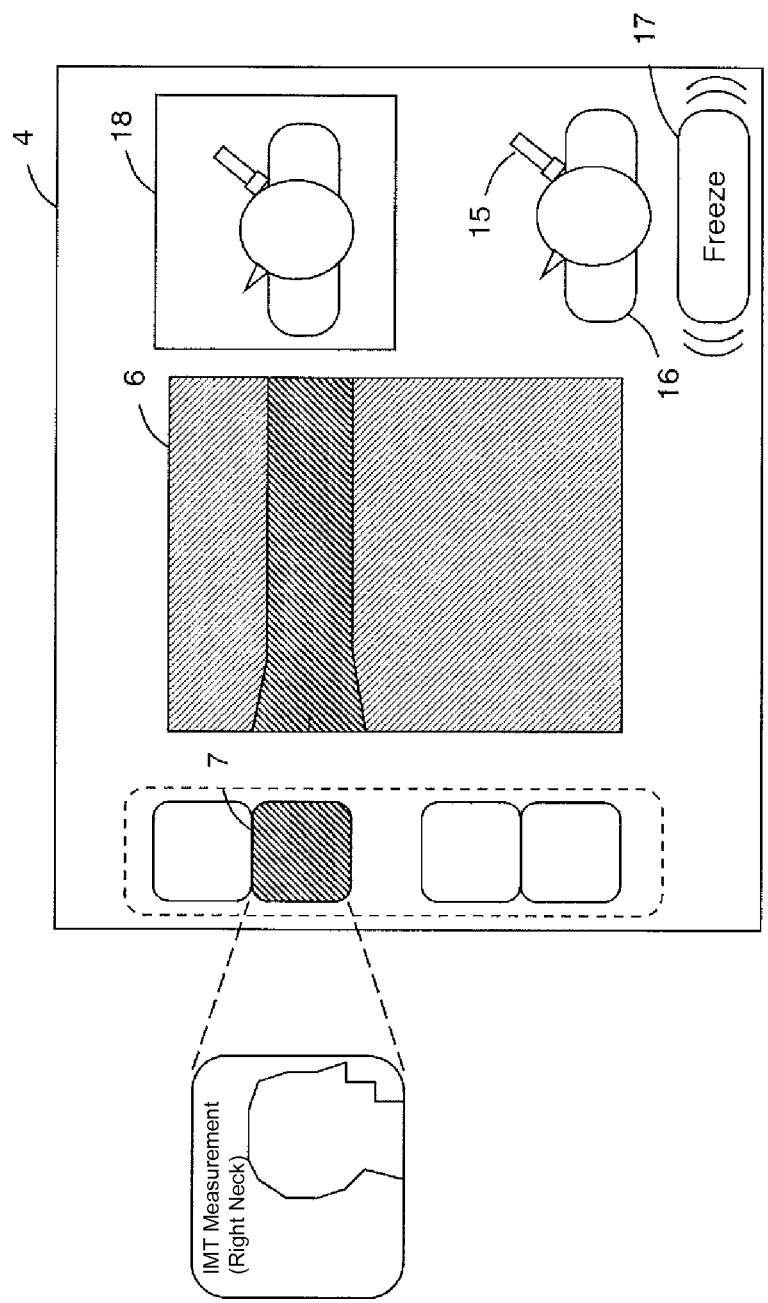
FIG. 6 is an explanatory view of the guide image and the workflow button (in blinking state).

For example, in the case of the guide image 18 in FIG. 5, the present angle (angle in a horizontal direction) of the probe icon 15 (ultrasound probe 3) is large, so that the "arrow" which instructs to incline the probe icon 15 in the horizontal direction is displayed. In this case, when the user inclines the ultrasound probe 3 in the horizontal direction according to the guide image 18 so that the ultrasound probe 3 coincides with the past angle information (or preset recommended angle), then the "arrow" vanishes from the guide image 18 as shown in FIG. 6. At this point, the subsequent diagnostic procedure (e.g., freeze) is displayed in the workflow button 17, and the workflow button 17 is put in the blinking state as described above.

Figure 7:
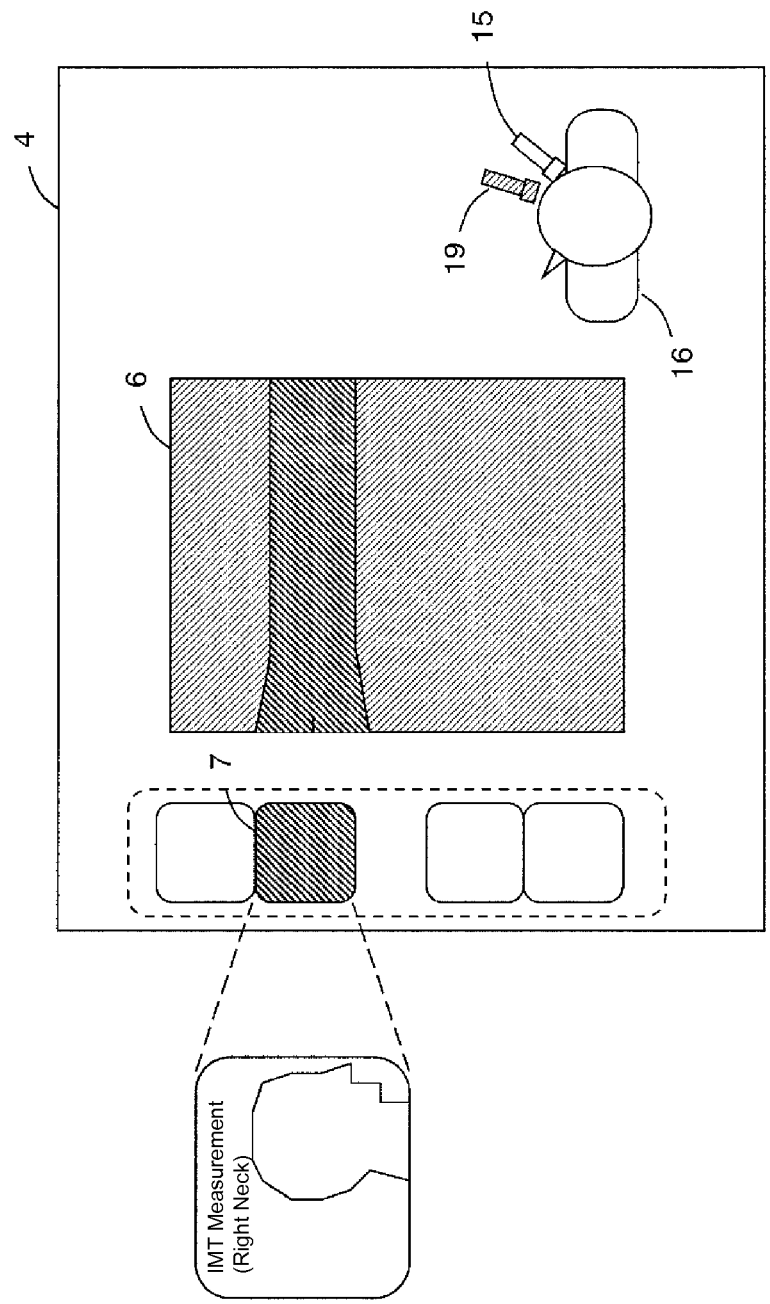
FIG. 7 is an explanatory view of a reference probe image.

The display processing section 12 has a function of displaying, when displaying the probe image on the monitor 4, a reference probe image 19 (probe icon displayed at an angle corresponding to the past angle information, i.e., reference probe icon 19) read from the storage section 13 with its configuration (such as color and form) different from that of the probe icon 15 (present probe icon 15). For example, FIG. 7 is a view showing an example of the reference probe icon 19. In the example of FIG. 7, the reference probe icon 19 is displayed in a color different from the present probe icon. When the past angle information is not stored in the storage section 13, the display processing section 12 may display on the monitor 4 the reference probe icon 19 at a recommended angle preset corresponding to the diagnostic mode.

The display processing section 12 also has a function of displaying, when displaying the past diagnosing image 6 (cine image) stored in the storage section 13, the past angle information stored in association with the past diagnosing image 6 (cine image) by the probe icon 15 on the monitor 4.

Further, the display processing section 12 may have a function of displaying on the monitor 4 an animation picture 20 for guiding a diagnostic procedure of the subject in the diagnostic mode. A operation button 21 of the animation picture 20 including "play/halt", "fast forward", and "fast rewind" may be displayed on the lower part of the animation picture 20 (see FIG. 8). Once the diagnostic procedure guided with the animation picture 20 is completed, an animation picture 20 for guiding the subsequent diagnostic procedure is displayed.

Not only an uninterrupted image but also a plurality of still pictures may be displayed as the animation picture 20.

According to such an ultrasound diagnostic apparatus 1 of the first embodiment, the acceleration sensor 5 provided on the ultrasound probe 3 is used so that an angle of the ultrasound probe 3 at the time of diagnosing the subject can be obtained and displayed without the necessity of placing a large-scale apparatus as in conventional cases.

More specifically, in the present embodiment, the acceleration information outputted from the acceleration sensor 5 provided on the ultrasound probe 3 is converted into angle information, so that an angle of the ultrasound probe 3 at the time of diagnosing the subject can be obtained and displayed on the monitor 4 without the necessity of a large-scale apparatus as in conventional cases (e.g., a magnetic field generator which cannot be mounted on the probe and can only be mounted on the bed). The acceleration sensor 5 is suitable to be mounted on the ultrasound probe 3 as it is easy to downsize.

In this case, as shown in FIG. 2 or FIG. 3, a subject image (body mark 16) corresponding to the diagnostic mode selected by a user (such as doctors and engineers) and a probe image (probe icon 15) placed at an angle corresponding to the angle information with respect to the subject image are displayed on the monitor 4 where the diagnosing image 6 is displayed. Accordingly, the user can sufficiently acquire information required for diagnosis from these images (images displayed on the monitor 4).

In the present embodiment, the button name of the button image (workflow button 17) displayed on the monitor 4 is changed in sequence in accordance with the diagnostic procedures of the subject as shown in FIG. 4, so that the user can implement the diagnostic procedures easily and appropriately with one button (workflow button 17). As shown in FIG. 6, once the diagnostic procedure shown with the button image (workflow button 17) on the monitor 4 is completed, the button (workflow button 17) is changed to represent a subsequent diagnostic procedure and is also displayed in the blinking state. This makes it possible to guide the user to proceed to the next diagnostic procedure.

Although the workflow button 17 is "displayed in the blinking state" in the case of indicating the subsequent diagnostic procedure, the configuration of the workflow button 17 is not limited thereto and any method such as change in color and luminance and making sound in combination with the color or luminance may be applicable as long as user's attention can be called.

In the present embodiment, when one diagnostic mode shifts to another diagnostic mode, the image data on the diagnosing image 6 obtained in the one diagnostic mode (diagnostic mode prior to mode shift) is associated with the angle information and this associated image data and angle information are stored. Therefore, in the case of referring to the past diagnosing image 6 (diagnosing image 6 obtained in the diagnostic mode) such as in the case of progress observation of the diagnostic region for example, the angle information at the time when the diagnosing image 6 was obtained can be acquired together with the diagnosing image 6, and this allows contrast observation with use of the images obtained under the same conditions (in the same diagnostic mode and at the same angle).

In the present embodiment, as shown in FIG. 7, when the present probe image (probe icon 15) is displayed and if the same diagnostic mode has been used for diagnosis before, then a reference probe image (reference probe icon 19) used for obtaining the diagnosing image 6 in the past diagnosis is displayed together with the present probe image. In this case, the reference probe image (reference probe icon 19) and the present probe image (probe icon 15) are distinguishably displayed with their configurations different from each other (such as different color and shape), so that the user can easily distinguish one from the other. The user can conduct diagnosis under the conditions same as the past diagnosis (in the same diagnostic mode and at the same angle) by making the reference probe image (reference probe icon 19) and the present probe image (probe icon 15) coincide with each other.

In the present embodiment, when a given subject has never been diagnosed in the same diagnostic mode before, a reference probe image (reference probe icon 19) is displayed at a recommended angle preset corresponding to the diagnostic mode (appropriate angle corresponding to the diagnostic mode). Therefore, the user can conduct diagnosis under appropriate conditions corresponding to the diagnostic mode by making the reference probe image (reference probe icon 19) and the present probe image (probe icon 15) coincide with each other.

In the present embodiment, as shown in FIG. 5 and FIG. 6, a guide image 18 indicating a direction to incline the ultrasound probe 3 in the diagnostic mode is displayed on the monitor 4. When the past angle information is stored in the storage section 13, the guide image 18 is appropriately generated based on the past angle information and the present angle information. Therefore, the user can easily conduct diagnosis under the conditions same as the past diagnosis (in the same diagnostic mode and at the same angle) according to the guide image 18. When the past angle information is not stored in the storage section 13, the guide image 18 is appropriately generated based on the recommended angle preset corresponding to the diagnostic mode (appropriate angle corresponding to the diagnostic mode) and the present angle information. Therefore, the user can easily conduct diagnosis under the appropriate conditions corresponding to the diagnostic mode according to the guide image 18.

Figure 8:
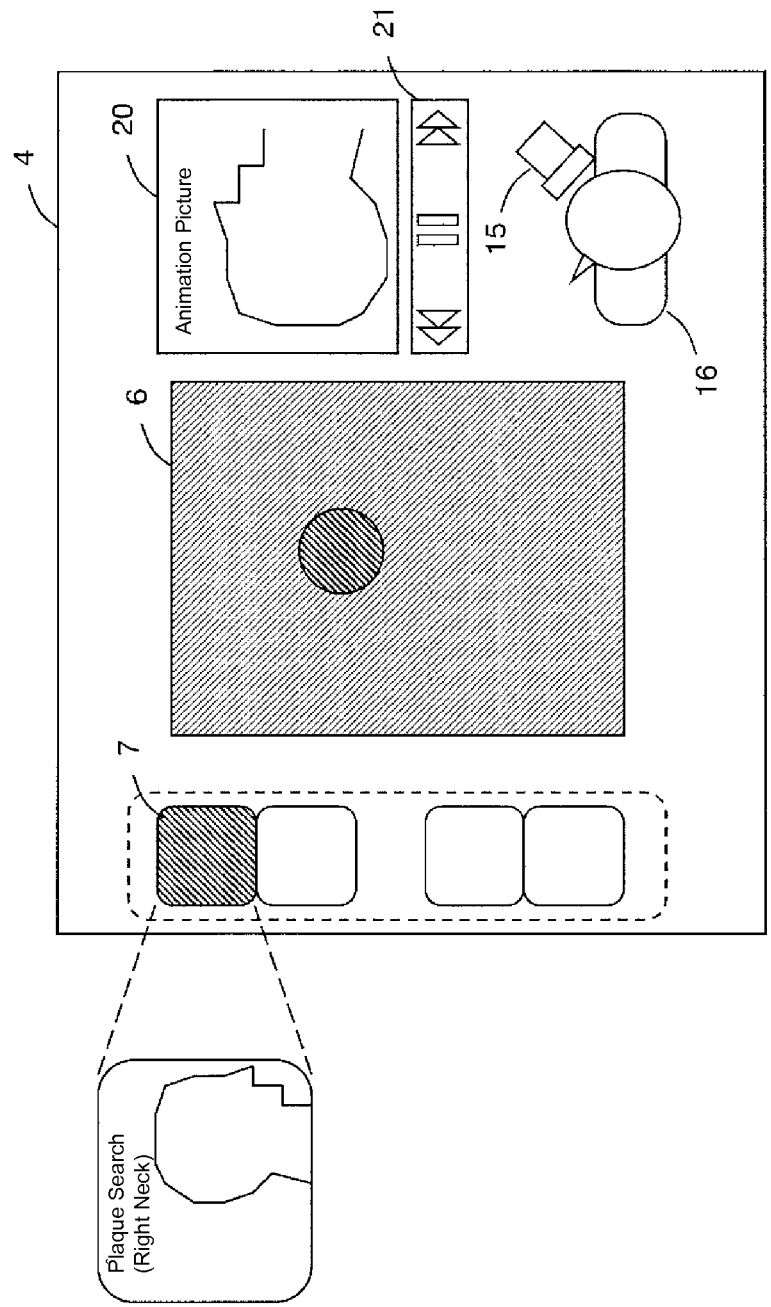
FIG. 8 is an explanatory view of an animation picture.

In the present embodiment, as shown in FIG. 8, an animation picture 20 for guiding a diagnostic procedure of the subject is displayed on the monitor 4. Once the diagnostic procedure guided with the animation picture 20 is completed, an animation picture 20 for guiding a subsequent diagnostic procedure is displayed. The user can implement the diagnostic procedures easily and appropriately according to the animation picture 20.

In the present embodiment, when the past diagnosing image 6 (cine image) is displayed on the monitor 4, the past angle information stored in association with the past diagnosing image 6 is displayed on the monitor 4. Therefore, the user can see the angle information in the past diagnosis together with the diagnosing image 6 obtained at the time of the past diagnosis.

In the present embodiment, through image analysis of the diagnosing image 6, the diagnostic mode in which the diagnosing image 6 was obtained is automatically determined, and an appropriate probe image (probe icon 15) corresponding to the diagnostic mode is displayed on the monitor 4. For example, when it is determined as a result of conducting image analysis of the diagnosing image 6 that the diagnostic mode is "plaque search", then the probe image (probe icon 15) for "plaque search" is displayed as shown in FIG. 3. Further, when it is determined as a result of conducting image analysis of the diagnosing image 6 that the diagnostic mode is "IMT measurement", then the probe image (probe icon) for "IMT measurement" is displayed as shown in FIG. 2.

In the present embodiment, through the image analysis of the diagnosing image 6, the diagnostic mode in which the diagnosing image 6 was obtained is automatically determined, and the image data on the diagnosing image 6 and the angle information are distributed and stored in an appropriate storage area corresponding to the diagnostic mode. For example, when it is determined as a result of conducting image analysis of the diagnosing image 6 that the diagnostic mode is "plaque search", then the image data on the diagnosing image 6 and the angle information are stored in the storage area for "plaque search". Further, when it is determined as a result of conducting image analysis of the diagnosing image 6 that the diagnostic mode is, for example, "IMT measurement", then the image data on the diagnosing image 6 and the angle information are stored in the storage area for "IMT measurement".

In the present embodiment, the monitor 4 is configured as a touch panel, so that the operability in selecting diagnostic mode is enhanced.

(Second Embodiment)

Hereinbelow, an ultrasound diagnostic system in a second embodiment of the present invention will be described. A description is mainly given of the difference of the ultrasound diagnostic system of the second embodiment from the first embodiment. Unless otherwise stated, the structure and operation of the present embodiment are similar to those of the first embodiment.

Figure 9:
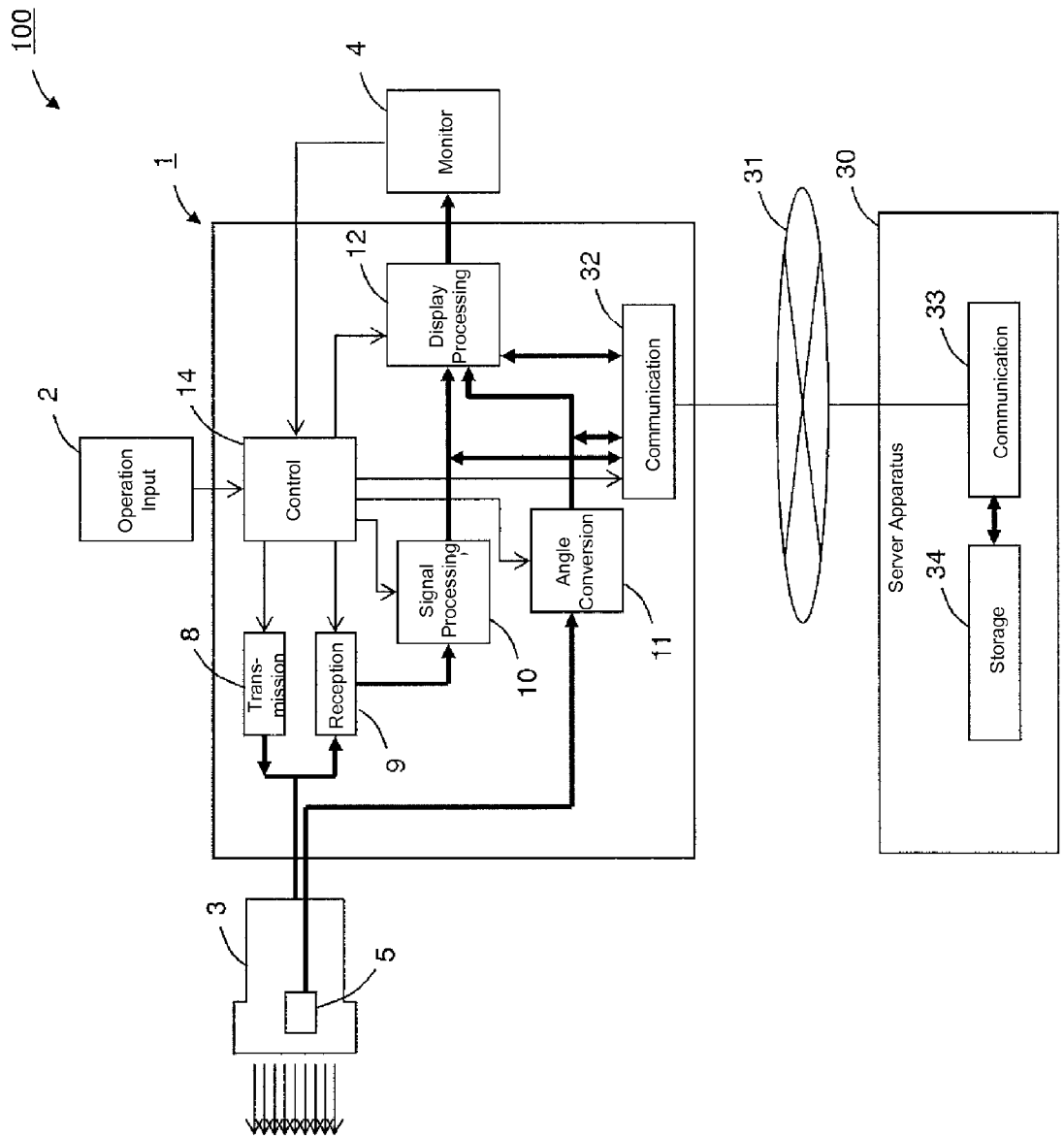
FIG. 9 is a block diagram of an ultrasound diagnostic apparatus in a second embodiment of the present invention.

FIG. 9 is a block diagram showing the structure of the ultrasound diagnostic system of the present embodiment. As shown in FIG. 9, an ultrasound diagnostic system 100 includes an ultrasound diagnostic apparatus 1 and a server apparatus 30. The ultrasound diagnostic apparatus 1 and the server apparatus 30 are communicably connected with each other via a network 31. In the present embodiment, the ultrasound diagnostic apparatus 1 does not include a high-capacity storage section 13. Instead, the ultrasound diagnostic apparatus 1 includes a communication section 32 which performs communication with the server apparatus 30. The server apparatus 30 includes a communication section 33 which performs communication with the ultrasound diagnostic apparatus 1, and a high-capacity storage section 34. In the present embodiment, when the diagnostic mode of the subject shifts to a subsequent diagnostic mode, image data on the diagnosing image 6 obtained in the diagnostic mode prior to mode shift are associated with the angle information, and the associated image data and angle information are transmitted to the server apparatus 30 and stored in the storage section 34 of the server apparatus 30.

In such an ultrasound diagnostic system 100 of the second embodiment, the same operation effect as the first embodiment may be implemented. That is, in the ultrasound diagnostic system 100 as in the ultrasound diagnostic apparatus 1 of first embodiment, an angle of the ultrasound probe 3 at the time of diagnosing the subject can be obtained and displayed on the monitor 4 without the necessity of a large-scale apparatus as in conventional cases (e.g., a magnetic field generator which cannot be mounted on the probe and can only be mounted on the bed), and the user can sufficiently acquire information required for diagnosis from the images displayed on the monitor 4.

Moreover, in the present embodiment, when one diagnostic mode shifts to another diagnostic mode, the image data on the diagnosing image 6 obtained in the one diagnostic mode (diagnostic mode prior to mode shift) are associated with the angle information, and this associated image data and angle information are transmitted from the ultrasound diagnostic apparatus to the server apparatus 30 and stored in the storage section 34 of the server apparatus 30. Therefore, in the case of referring to the past diagnosing image 6 (diagnosing image 6 obtained in the diagnostic mode) such as in the case of progress observation of the diagnostic region for example, the ultrasound diagnostic apparatus 1 can acquire the angle information at the time when the diagnosing image 6 was obtained together with the diagnosing image 6 from the storage section 34 of the server apparatus 30, and this allows contrast observation with use of the images obtained under the same conditions (in the same diagnostic mode and at the same angle).

Since the carotid artery exists on both the side surfaces of the neck, it is hard to apply the probe on the subject who faces the front and stays on his/her back. Moreover, if the angle of the head changes in every diagnosing operation, it becomes difficult to reproduce the diagnosing position at a precise angle. Accordingly, the head of the subject needs to be inclined at a constant angle, though it is not easy for the subject to incline his/her head at a constant angle.

Figure 10:
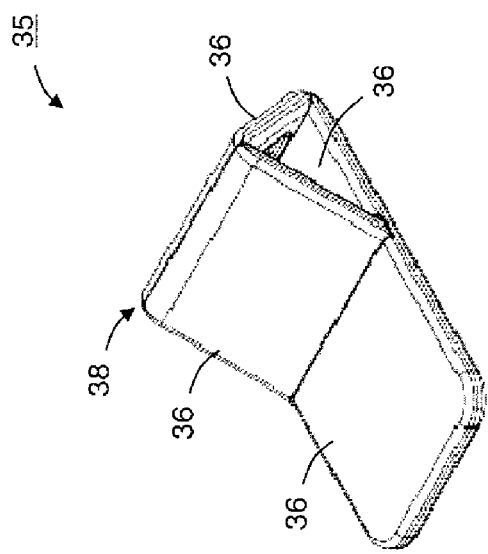
FIG. 10 is a perspective view of a folding pillow (in use state).
Figure 11:
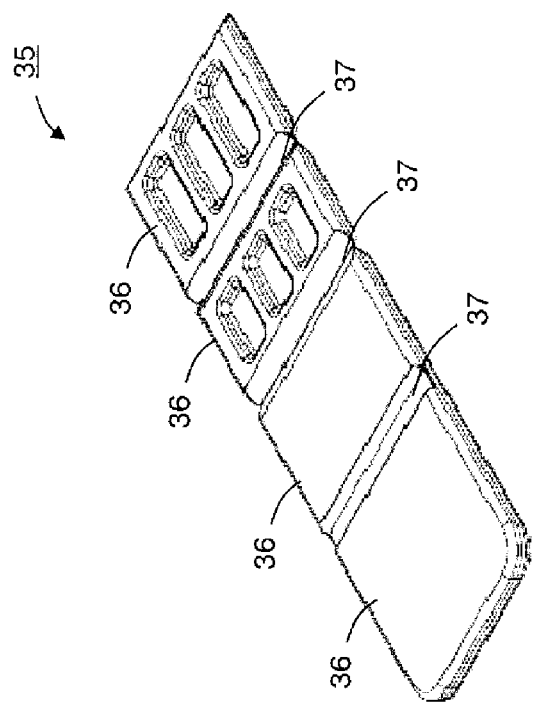
FIG. 11 is a perspective view of the folding pillow (in stored state).
Figure 12:
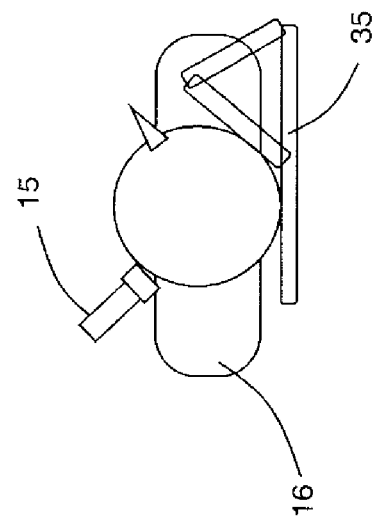
FIG. 12 is a schematic explanatory view of the folding pillow in use state.

Accordingly, to improve the operability and reproducibility of diagnosis, it is effective for the ultrasound diagnostic system 100 to use a folding pillow 35 which is to be put under the head of the subject during implementation of diagnosis (see FIG. 12). FIG. 10 is a perspective view showing the folding pillow 35 in use state (folded state), and FIG. 11 is a perspective view showing the folding pillow 35 in stored state (extended state). As shown in FIG. 10 and FIG. 11, the folding pillow 35 is composed of a series of four plate-like sections 36, the adjacent plate-like sections 36 being coupled to each other through an end portion 37 (coupled section). The folding pillow 35 is manufactured from, for example, materials such as low foaming urethane.

For putting the folding pillow 35 in use state, the folding pillow 35 is folded so as to form a triangular prism-shaped three-dimensional pillow section 38 with use of three plate-like sections 36 as shown in FIG. 10. The subject puts his/her head on the remaining one plate-like section 36 while inclining his/her head so that one side of the head is in contact with the three-dimensional pillow section 38. Accordingly, as shown in FIG. 12, it becomes possible to easily keep the state of inclining the head at a constant angle, and thereby the operability and reproducibility of diagnosis can be enhanced. After use, the folding pillow 35 is put in extended state as shown in FIG. 11. Thus, the folding pillow 35 can be stored in a small storage space.

Although the embodiments of the present invention have been described above in an illustrative manner, it should be understood that the scope of the present invention is not limited to the embodiments described, and modifications and variations depending on purposes are possible within the scope stated in the claims.

Although the preferable embodiments of the present invention conceivable at the present moment have been described above, it should be understood that various modifications are possible for the embodiments disclosed and unless departing from the spirit and scope of the invention, such modifications are intended to be embraced in the scope of the appended claims.

INDUSTRIAL APPLICABILITY

As disclosed above, the ultrasound diagnostic apparatus according to the present invention has an effect that the angle of an ultrasound probe at the time of diagnosing a subject can be obtained and displayed without the necessity of placing a large-scale apparatus as in conventional cases. The ultrasound diagnostic apparatus according to the present invention is mainly applicable to and useful in the medical field.

REFERENCE SIGNS LIST

1 Ultrasound diagnostic apparatus
2 Operation input section
3 Ultrasound probe
4 Monitor
5 Acceleration sensor
6 Diagnosing image
7 Diagnostic mode button
8 Transmission section
9 Reception section
10 Signal processing section
11 Angle conversion section
12 Display processing section
13 Storage section
14 Control section
15 Probe icon
16 Body mark
17 Workflow button
18 Guide image
19 Reference probe icon
20 Animation picture
21 Operation button
30 Server apparatus
31 Network
32 Communication section
33 Communication section
34 Storage section
35 Folding pillow
36 Plate-like section
37 End portion
38 Three-dimensional pillow section
39 Display area
100 Ultrasound diagnostic system

The invention claimed is:

1. An ultrasound diagnostic apparatus, comprising:
an ultrasound probe;
a sensor provided on the ultrasound probe which outputs sensor information for use in obtaining an angle of the ultrasound probe relative to a gravity direction at a time of diagnosing a subject;
a memory comprising a plurality of storage areas corresponding to a plurality of diagnostic modes, respectively; and
a processor which is configured to perform control to:
convert the sensor information output by the sensor provided on the ultrasound probe into angle information of the ultrasound probe;
associate, when a diagnostic mode for diagnosing the subject with the ultrasound probe shifts to a subsequent diagnostic mode in accordance with an operation by an operator, image data of a diagnosing image obtained in the diagnostic mode prior to mode shift with the angle information, and store the associated image data and angle information in the memory in the storage area corresponding to the diagnostic mode in which the image data was obtained; and
generate a probe image indicating the ultrasound probe as a schematic graphic and a subject image indicating the subject as a schematic graphic, display the subject image, and display the probe image at an angle corresponding to the angle information in a region including the subject image on a display, wherein the probe image and the subject image correspond to a specific diagnostic mode and are generated so as to have display features which are specific to the corresponding diagnostic mode;

wherein the processor is further configured to perform control to:
display the subject image corresponding to the diagnostic mode after the mode shift, the subject image having the display features which are specific to the corresponding diagnostic mode;
when past angle information is stored in the memory in the storage area corresponding to the diagnostic mode after the mode shift, display a reference probe image at an angle corresponding to the past angle information which is read from the storage area in the memory corresponding to the diagnostic mode after the mode shift; and
when the past angle information is not stored in the memory in the storage area corresponding to the diagnostic mode after the mode shift, display the reference probe image at a preset angle corresponding to the diagnostic mode after the mode shift, wherein the preset angle is an angle which has been determined in advance to be appropriate for the corresponding diagnostic mode;
wherein the processor is further configured to perform control to display, on the display, a plurality of buttons corresponding to the plurality of the diagnostic modes, respectively;
wherein the plurality of buttons are operable by the operator to select one of the diagnostic modes; and
wherein when the diagnostic mode is shifted in accordance with operation of one of the buttons, the processor associates the image data of the diagnosing image obtained in the diagnostic mode prior to mode shift with the angle information, and stores the associated image data and the angle information in the memory in the storage area corresponding to the diagnostic mode in which the image data was obtained.

2. The ultrasound diagnostic apparatus according to claim 1, wherein the processor is configured to perform control to set the region over the subject image and display the probe image as if in contact with the subject image on the display.

3. The ultrasound diagnostic apparatus according to claim 1, wherein:
the sensor is an acceleration sensor which outputs acceleration information of the ultrasound probe as information for use in obtaining the angle of the ultrasound probe, and
the processor is configured to perform control to convert the acceleration information into angle information of the ultrasound probe.

4. The ultrasound diagnostic apparatus according to claim 1, wherein the processor is further configured to perform control to display, on the display, a button image whose button name is changed in sequence in accordance with procedures performed on the subject.

5. The ultrasound diagnostic apparatus according to claim 4, wherein once a diagnostic procedure indicated by the button name is completed, the processor is configured to perform control to display, on the display, a button image representing a subsequent diagnostic procedure in a blinking state.

6. The ultrasound diagnostic apparatus according to claim 1, further comprising a monitor which is operable to select the diagnostic mode.

7. The ultrasound diagnostic apparatus according to claim 1, wherein:

the processor is further configured to perform control to display, on the display, a guide image indicating a direction to incline the ultrasound probe in the diagnostic mode,
when the past angle information is stored in the memory, the guide image is generated based on the past angle information read from the memory and present angle information converted from the sensor information, and
when the past angle information is not stored in the memory, the guide image is generated based on the preset angle corresponding to the diagnostic mode and the present angle information converted from the sensor information.

8. The ultrasound diagnostic apparatus according to claim 1, wherein:
the processor is further configured to perform control to display, on the display, an animation picture for guiding a diagnostic procedure of the subject in the diagnostic mode, and once the diagnostic procedure guided with the animation picture is completed, to display an animation picture for guiding a subsequent diagnostic procedure.

9. The ultrasound diagnostic apparatus according to claim 1, wherein, when displaying a past diagnosing image stored in the memory, the processor is configured to perform control to display, on the display, past angle information stored in association with the past diagnosing image.

10. The ultrasound diagnostic apparatus according to claim 1, wherein the processor is further configured to perform image analysis of the diagnosing image of the subject to determine a diagnostic mode in which the diagnosing image was obtained.

11. The ultrasound diagnostic apparatus according to claim 10, wherein:
the processor is configured to distribute and store the image data of the diagnosing image and the angle information in the storage area corresponding to the determined diagnostic mode.

12. The ultrasound diagnostic apparatus according to claim 1, wherein the display comprises a touch panel, and selection of the diagnostic mode is achieved by a touch operation performed on the touch panel.

13. An ultrasound diagnostic system, comprising:
a server which has a memory comprising a plurality of storage areas corresponding to a plurality of diagnostic modes, respectively; and
an ultrasound diagnostic apparatus which is capable of communicating with the server via a network,
wherein the ultrasound diagnostic apparatus includes:
an ultrasound probe;
a sensor provided on the ultrasound probe which outputs sensor information for use in obtaining an angle of the ultrasound probe at a time of diagnosing a subject; and
a processor which is configured to perform control to:
convert the sensor information output by the sensor provided on the ultrasound probe into angle information of the ultrasound probe;
associate, when a diagnostic mode for diagnosing the subject with the ultrasound probe shifts to a subsequent diagnostic mode in accordance with an operation by an operator, image data of a diagnosing image obtained in the diagnostic mode prior to mode shift with the angle information, and store the associated image data and angle information in the memory in the storage area corresponding to the diagnostic mode in which the image data was obtained; and generate a probe image indicating the ultrasound probe as a schematic graphic and a subject image indicating the subject as a schematic graphic, display the subject image, and display the probe image at an angle corresponding to the angle information in a region including the subject image on a display, wherein the probe image and the subject image correspond to a specific diagnostic mode and are generated so as to have display features which are specific to the corresponding diagnostic mode;

wherein the processor is further configured to perform control to:

display the subject image corresponding to the diagnostic mode after the mode shift, the subject image having the display features which are specific to the corresponding diagnostic mode;

when past angle information is stored in the memory in the storage area corresponding to the diagnostic mode after the mode shift, display a reference probe image at an angle corresponding to the past angle information which is read from the storage area in the memory corresponding to the diagnostic mode after the mode shift; and when the past angle information is not stored in the memory in the storage area corresponding to the diagnostic mode after the mode shift, display the reference probe image at a preset angle corresponding to the diagnostic mode after the mode shift, wherein the preset angle is an angle which has been determined in advance to be appropriate for the corresponding diagnostic mode;

wherein the processor is further configured to perform control to display, on the display, a plurality of buttons corresponding to the plurality of the diagnostic modes, respectively;

wherein the plurality of buttons are operable by the operator to select one of the diagnostic modes; and wherein when the diagnostic mode is shifted in accordance with operation of one of the buttons, the processor associates the image data of the diagnosing image obtained in the diagnostic mode prior to mode shift with the angle information, and stores the associated image data and the angle information in the memory in the storage area corresponding to the diagnostic mode in which the image data was obtained.

* * * * *